United States Patent [19]

Gmelin et al.

[11] Patent Number: 4,783,174
[45] Date of Patent: Nov. 8, 1988

[54] DIFFERENTIAL ISOPERIBOL SCANNING CALORIMETER

[75] Inventors: Eberhard Gmelin, Leonberg; Karl Ripka, Simmozheim; Susanne Lederer, Leingarten, all of Fed. Rep. of Germany

[73] Assignee: Max-Planck-Gesellschaft zur Foerderung der Wissenschaften e.v., Fed. Rep. of Germany

[21] Appl. No.: 897,530

[22] Filed: Aug. 18, 1986

[30] Foreign Application Priority Data

Aug. 16, 1985 [DE] Fed. Rep. of Germany ....... 3529489

[51] Int. Cl.$^4$ ...................... G01K 17/00; G01N 25/20
[52] U.S. Cl. ......................................... 374/33; 374/11; 374/31
[58] Field of Search ........................ 374/33, 31, 34, 10, 374/11, 12, 13

[56] References Cited

U.S. PATENT DOCUMENTS

| 3,643,491 | 2/1972 | Dell et al. | 374/11 |
| 4,255,961 | 3/1981 | Biltonen et al. | 374/11 |

FOREIGN PATENT DOCUMENTS

| 0027496 | 3/1978 | Japan | 374/11 |
| 0209158 | 10/1985 | Japan | 374/31 |

OTHER PUBLICATIONS

Moses et al., "Simple Calorimetric System for the T Range 3—300K w/online Computer", Rev. Sci. Instrum., vol. 48, No. 8 (Aug. 1977), pp. 1098–1103.
Durek et al., "Simple Specific Heat Measurements at Low Temp.", J. Phys. E. Sci. Instrum., vol. 5, No. 5 (May 1972), pp. 424–428.
Nichols et al., "Testing of an Auto. Temp. Recording System for an Isoperibolic Solution Calorimeter", Chemica Scripta., vol. 9, No. 3 (1976), pp. 110–113.
Forgan et al., "Heat Capacity Cyrostat & Novel Methods of Analysis for Small Specimens in the 1.5–10K Range", Rev. Sci. Instrum., vol. 51, No. 4 (Apr. 1980), pp. 411–417.
Bachman et al., "Heat Capacity Measurements on Small Samples at Low Temp.", Rev. Sci. Instrum., vol. 43, No. 3 (Feb. 1972), pp. 205–214.
Fagaly et al., "A Modified Heat Pulse Method for Determining Heat Capacities at Low Temperatures", Rev. Sci. Instru., vol. 48, No. 11 (Nov. 1977), pp. 1502–1503.
Hsieh et al., "Twin Slope Method of Measurement of Specific Heat & Coating Absorptance of Solid Materials", Rev. Sci. Instrum., vol. 53, No. 5 (May) 1982, pp. 684–689.
Franz X. Eder: Arbeitsmethoden der Thermodynamik; vol. 11, 1983, pp. 213–220; published by: Springer—Verlag, Berlin, 1983.
Rev. Sci. Instrum., 51(8), Aug. 1980, pp. 1030–1036, Griffing et al., "An Automated Relaxation Calorimeter with Extended Temperature Range".

Primary Examiner—William A. Cuchlinski, Jr.
Assistant Examiner—Thomas B. Will
Attorney, Agent, or Firm—Handal & Morofsky

[57] ABSTRACT

A continuously operating non-adiabatic, differential calorimeter, i.e., a differential isoperibol scanning calorimeter, for measuring the heat capacity of small samples typically from 10 milligrams to 50 milligrams, in a temperature range from about 1 Kelvin to about 100 Kelvin.

15 Claims, 3 Drawing Sheets $$T_i(t) = T_0 + T_{im} e^{-(t/t_i^*)} \; ; \; t_i^* = \frac{C_i}{K_i}$$

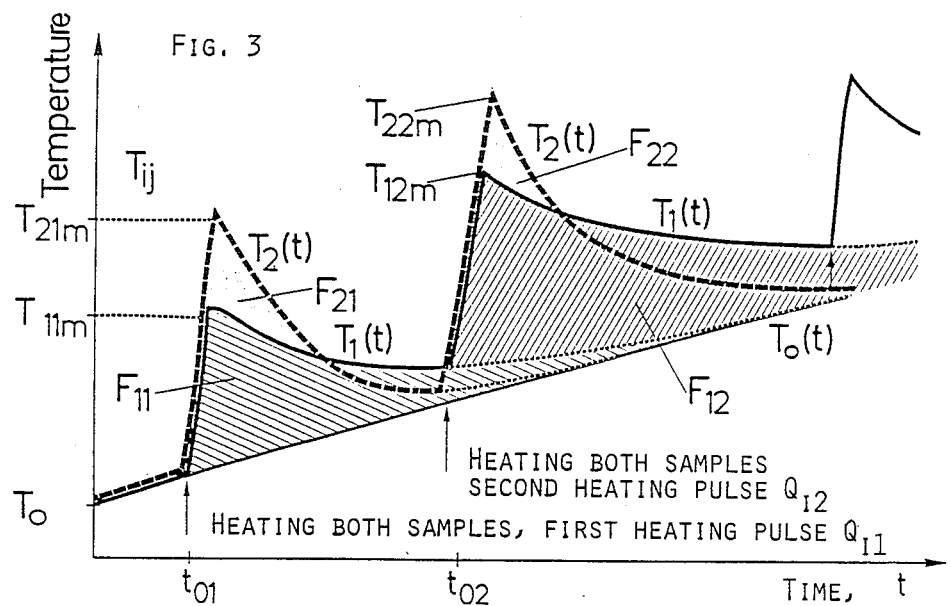
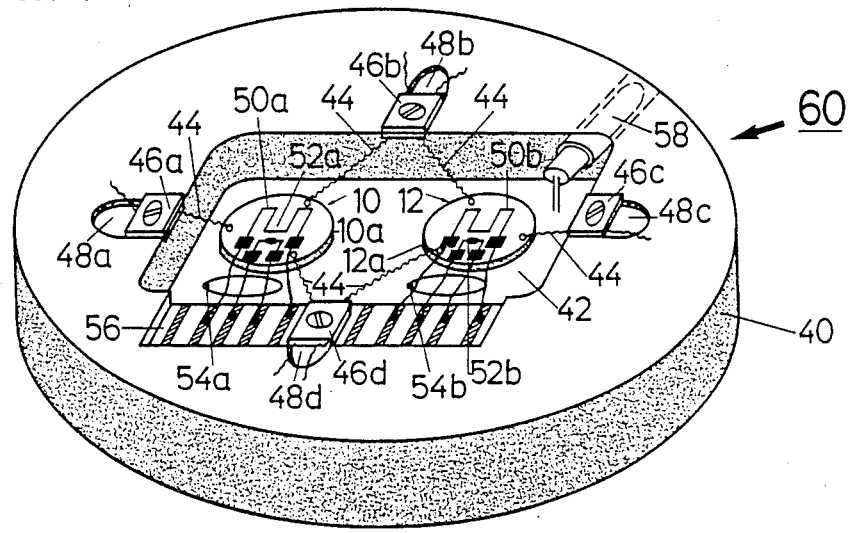

DIFFERENTIAL ISOPERIBOL SCANNING CALORIMETER

The present invention relates to measuring thermal parameters of a material, more specifically to measuring the heat capacity and the specific heat of a material within a large temperature range.

BACKGROUND OF THE INVENTION

Thermal analyses encompass an extremely wide spectrum of activities and a large variety of experimental methods. The key thermal property measured is the heat capacity of a sample of known mass, from which the specific heat of the sample material, which may be solid or liquid, can be calculated and basic thermodynamic functions such as phase transition enthalpies as well as reaction kinetics can be derived. Measurements of this type have been made in a very large temperature range from near absolute zero, i.e. 0 K. (Kelvin) to very high temperatures well above 1500 K. However, the overwhelming number of investigations in this branch of science is still restricted to one decade in temperature, namely the range from about 120 K. to about 1500 K.

Thermal analysis in the temperature range above 120 K. has seen a rapid development in instrumentation and automatization in the last ten to twenty years, while calorimetic experiments below 120 K. have been neglected somewhat and measurements in this temperature range are still a domain of a few cryogenic laboratories. The reason for this development of the art of calorimetric instruments is mainly due to the fact that the specific heat varies by many orders of magnitude in this temperature range.

A review of the state of the art of calorimetry is found in the book of W. Hemminger and G. Höhne "Grundlagen der Kalorimetrie" Verlag Chemie, Weinheim/New York, 1979. The definition of terms of this book are also used in this specification:

Twin calorimeter: A pair of measuring systems which are as equal as possible are operated symmetrically in a homogeneous environment. Measurement and reference samples are used which are as equal as possible with respect to their heat capacity, configuration, heat conductivity, heat transfer to the measuring system and so on.

Isoperibol operation: Isoperibol operation of a calorimeter means that the calorimeter is operated in an environment of a given, generally constant temperature from which the temperature of the measuring system differs as much as possible. The measuring system is coupled to the environment by a well defined heat conducting path or heat resistance of finite magnitude so that the heat exchange between the measuring system and the environment depends in a well defined manner only from the temperature of the measuring system and the temperature of the environment.

Scanning operation: The temperature of the measuring system of the calorimeter or the temperature of its environment is raised proportionally linearly with respect to time to time by means outside of the calorimeter and its environment.

Power compensated twin calorimeters (DPSC) are known which are operated in an isoperibolic scanning mode (Hemminger/Höhne, l.c. page 72, 73). These calorimeters comprise a pair of individual measuring systems in a common environment, the temperature of which is kept constant. The temperatures of the measuring systems are kept equal and raised linearly with time by individual regulated heating devices. The difference of the heating powers supplied by the heating devices to the individual measuring systems constitutes the measured magnitude.

Further differential or twin heat conductance calorimeters are known (Hemminger/Höhne l. c. page 181) which may be operated in an environment scanning mode (Hemminger/Höhne l. c. page 192, 193).

SUMMARY OF THE INVENTION

The present invention provides a new type of calorimetric method and a new type of calorimeter which are specifically suited but not limited to low temperature calorimetry (L.T.C.). They meet all requirements needed to determine heat capacities of samples in the 10 milligram range between 4 K. and 300 K. with high accuracy.

An essential aspect of the invention is the combination of the following features:
1. Isoperibol conditions;
2. Differential arrangement;
3. Continuous gradual heating of the environment.

Further important, preferred features are:
4. Use of calibration-independent thermometers;
5. Automation and platform-type sample holder;
6. Simple and easy-to-handle cryogenic equipment.

Isoperibol conditions (heat leak methods) were scarcely used at temperatures above 4 K. Only a few differential calorimeters are known in the art, and none of them is well adapted to small sample measurements.

The present method and apparatus are well suited for rapid calorimetric measurements of small samples of solids and liquids (which may be sealed in a thin-walled glass container), having masses in the milligram range, with accuracies of few percent. Thus, no more than about 10 seconds to a maximum of several minutes are needed for a measuring point at a given sample temperature.

The method and calorimeter according to the invention are specifically suited for temperatures from about 1 K. to about 100 K. Not only the use of the isoperibolic relaxation-time calorimetry at temperatures above about 10 K. is new but also the combination with the scanning mode at temperatures below 100 K.

BRIEF DESCRIPTION OF THE DRAWINGS

FIG. 3 is a temperature-time diagram showing typical temperature signals as they are obtained with the calorimeter of FIG. 1;

FIG. 4 is an isometric view of the bottom side of a typical measuring system of a calorimeter according to one embodiment of the invention.

DESCRIPTION OF A PREFERRED EMBODIMENT

Figure 1:
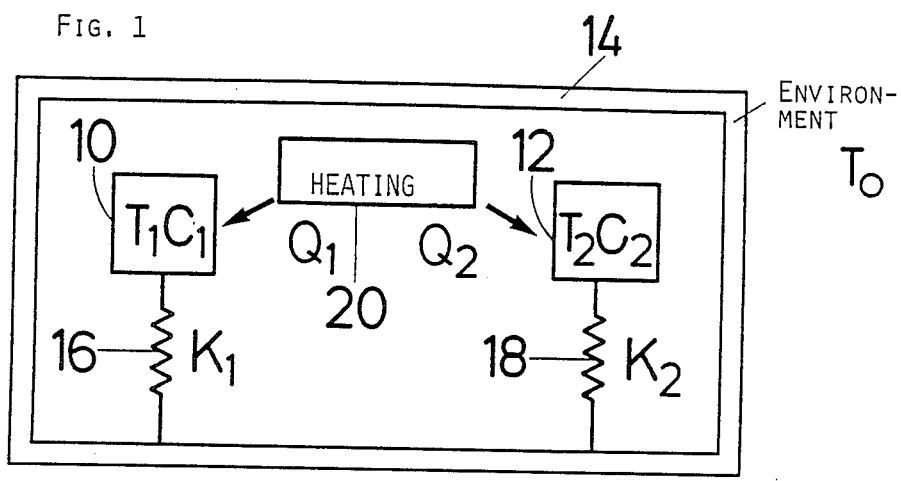
FIG. 1 is a schematic diagram, partially in block form, for explaining the principle of the differential isoperibolic scanning calorimeter according to one embodiment of the invention.

As shown schematically in FIG. 1, the method according to one embodiment of the invention for measuring the heat capacity of a sample makes use of a measuring system 10 and a reference system 12 which are positioned in a common environment 14 which has a practically infinite heat capacity and a well defined, regulated temperature $T_0$. A heat conducting path or "heat resistor" 16 which has a well defined heat resistance $K_1$ couples the measuring system 10 to the environment 14. In a similar way, a well defined second heat conducting path or heat resistor 18 having a heat resistance $K_2$ couples the reference system 12 to the environment 14. The heat coupling between the measuring system 10 and the reference system 12 should be sufficiently small so that it can be neglected.

The measuring system 10 has a heat capacity $C_1$ which includes the heat capacity of the sample to be measured (measuring sample), and the heat capacity of the sample support. The heat capacity of the sample support should be as small as possible relative to the heat capacity of the sample. The temperature of the measuring system is $T_1$ and it is assumed that essentially a temperature equilibrium exists between the sample support and the sample and within the sample, i.e., that the time needed for establish a temperature equilibrium between the sample support, the sample and within the sample is short relative to the changes of the temperature of the measuring system relative to the environment 14 during the measuring procedure.

The reference system 12 has a heat capacity $C_2$ and a temperature $T_2$ and properties as discussed above with reference to the measuring system 10.

Figure 2:
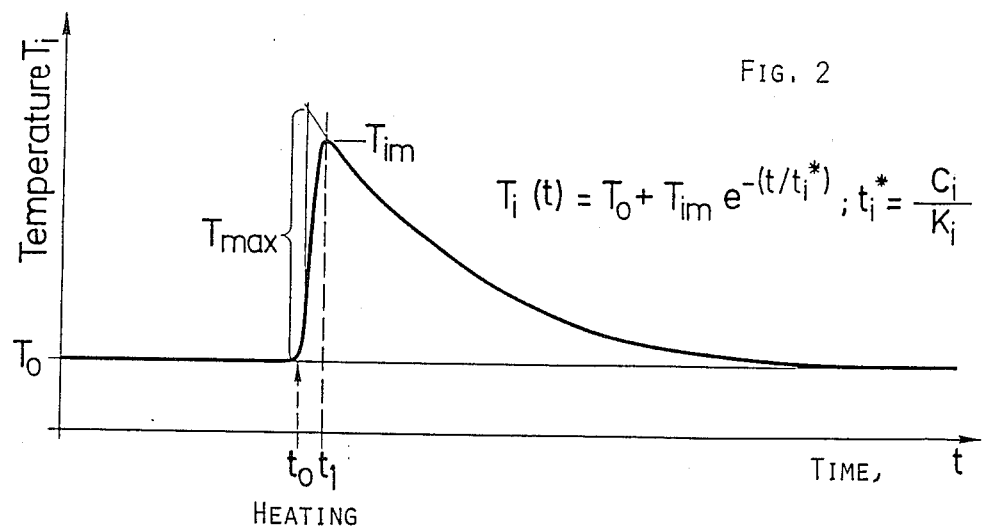
FIG. 2 is a temperature (T) vs time (t) diagram for explaining the principle of the relaxation time calorimetry.

Referring now to FIG. 2, if heat energy 20 of the amount $Q_i$ (i=1 for the measuring system 10; i=2 for the reference system 12 as shown in FIG. 1) is supplied to the measuring system 10 or to the reference system 12 within a period of time $t_1-t_0$, which is short compared with the time constant $t_i^*$ resulting from $C_i$ and $K_i$, i.e., $C_i/K_i$, the temperature $T_i$ of the respective system varies as shown in FIG. 2. Thus, $T_i$ increases from an initial temperature value $T_0$ which is equal to the temperature of the environment to a maximum value $T_{im}$ within the period of time $t_1-t_0$ and then decreases exponentially to $T_0$, corresponding to the equation $$T_i(t) = T_0 + (T_{im} - T_0)e^{-(t/t_i^*)}$$

wherein $t_i^* = C_i/K_i$, the time constant of the system i.

An environment temperature $T_0(t)$ varying with time is used in the method according to the invention rather than a constant environment temperature $T_0$. More specifically, the environment temperature $T_0(t)$ is preferably increased linearly with time as the line $T_0(t)$ in FIG. 3 shows.

During the variation of the environment temperature $T_0(t)$, heat energies having the amounts $Q_{11}$ and $Q_{21}$ are supplied to the measuring system 10 and the reference system 12, respectively (the first index denotes the system as the above mentioned index i, the second is the number of the heat pulse applied), as explained above with reference to FIG. 2. Thus, the first heat pulses raise the temperature $T_1$ of the measuring system to a first maximum value $T_{11m}$ and the temperature of the reference system to corresponding first maximum value $T_{21m}$, thereafter the temperatures of the measuring and reference systems decrease as described with reference to FIG. 2 exponentially with the time constants $t_1^*$ and $t_2^*$, respectively. At a later point of time $t_{02}$ heat energies with the amounts $Q_{12}$ and $Q_{22}$ are applied to the measuring system and the reference system, respectively, the amounts $Q_{12}$ and $Q_{22}$ being preferably equal to $Q_{11}$ and $Q_{21}$, respectively. The same applies to the amounts of the heat energies $Q_{1n}$, $Q_{2n}$ (n=3, 4 . . .) of the following heat pulses. Since the temperature $T_0(t)$ of the environment is higher at the point of time $t_{02}$ than at the time $t_{01}$ of the application of the first heat pulses, the maximum temperatures $T_{12m}$ and $T_{22m}$ of the measuring system 10 and the reference system 12, respectively will be higher than the maximum temperatures $T_{11m}$ and $T_{21m}$, respectively.

The heat capacity $C_1$ and, thus, the heat capacity $C_x$ of the sample can be calculated from the heat relaxation time $t_1^*$, the heat capacity $C_2$, and the portion $C_{1p}$ which the sample support contributes to the heat capacity $C_1$. The values of $C_2$ and $C_{1p}$ are obtained by calibration. The following relationships exist:

$$C_x = C_1^{kor} - C_{1p}$$

wherein $C_1^{kor}$ is a corrected, true value of $C_1$ which is obtained from a comparison of an experimentally determined value of $C_2$ with an exact value $C_2^{lit}$ known from the literature, by $$C_1^{kor} = (C_2^{lit}/C_2)C_1.$$

$$C_i = K_i t_i^*.$$

The relaxation times $t_i^*$ are calculated according to FIG. 3 from the following equation by an iteration procedure $$(T_i(t) - T_0) = ((T_{ij}) - (T_0 + (st_i^*))e^{-(t/t_i^*)} + st_i^*((t-/t_i^*) - 1)$$

wherein s is the scanning rate. The relaxation time $t_i^*$ can be calculated more precisely from the area $F_{ij}$ below the cooling curve by the following integral of the above equation and again iteration, in the first order approximation:

$$F_{ij} = \int_{t_{01}}^{t_{02}} (T_i(t) - T_0)dt$$
$$= (T_{ij} - (T_0 + st_i^*))t_i^*(1 - e^{-(t_{02}-t_{01})/t_i^*}).$$

The conditions are preferably chosen, so that, at least within an order of magnitude $$C_1 = C_2$$
$$K_1 = K_2$$
$$Q_1 = Q_2.$$

If the condition $C_1 = C_2$ cannot be fulfilled, the setup is preferably chosen so that the area $F_{1n}$ is at least approximately equal to the area $F_{2n}$.

It is not essential, how the temperatures $T_0$, $T_1$ and $T_2$ are measured. Preferred is a measurement of $T_0$ and measurements of the temperature differentials $T_1-T_2$, and $T_2-T_0$. Alternatively other temperature differentials can be measured or all three temperatures can be measured directly.

The period of time between two subsequent heat pulses, i.e., between $t_{02}$ and $t_{01}$ in FIG. 3, is preferably chosen equal to one times to three times, preferably two times, of $t_1^*$. This means that the temperatures decreases after a heat pulse at least to (1/e) times the maximum value produced by the preceding heat pulse before the next heat pulse is applied. Since the temperatures decrease in accordance with an exponential function, the contributions of any preceding heat pulse can be easily taken into account in the calculations as known per se in the art.

Figure 5:
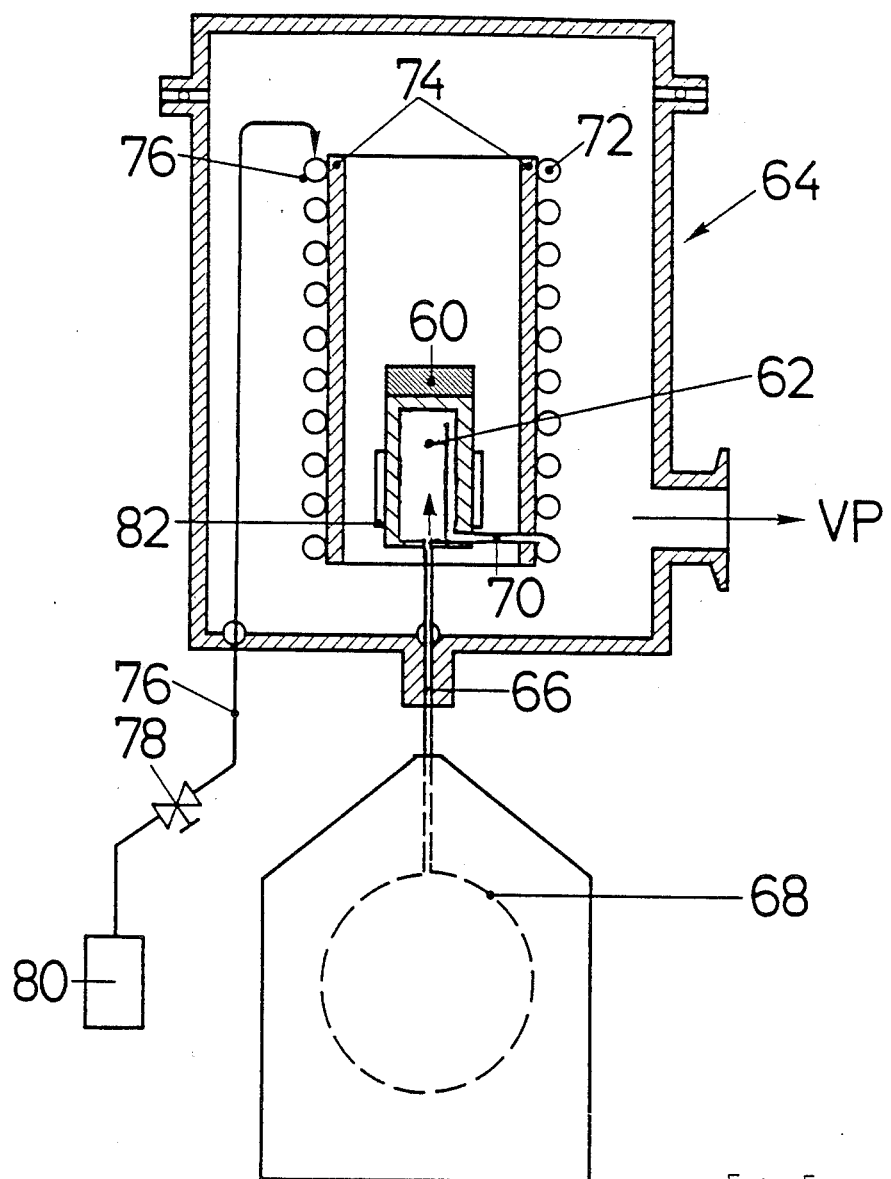
FIG. 5 is a simplified sectional view of a cryostat system in which the measuring system of FIG. 4 may be used during measurements.

Reference is now made to FIGS. 4 and 5, which show the essential portions of a isoperibolic twin scanning calorimeter according to one embodiment of the invention.

FIG. 4 shows the measuring system 60 of the calorimeter, which embodies the present invention. The measuring system comprises a solid, disc-shaped block 40 which constitutes the environment of the measuring system and may be made of copper. The block 40 has an essentially rectangular cut-out or hole 42 in which the measuring system 10 and the reference system 12 are supported independently of each other and thermally decoupled from each other. The measuring system 10 and the reference system 12 each comprise a sample holder 10a and 12a, respectively, which should have a heat capacity as small as possible and are therefore preferably made of a material with a high Debye temperature. In the present embodiment, the sample holders 10a and 12a each comprise a disk which is made of sapphire and has a thickness of about 0.15 mm. Alternatively, the sample holders may be made of another material, e.g., germanium.

Each of the sample holder disks 10a, 12a is mechanically supported from the block 40 by three filaments 44 made of a material of low heat conductivity, as wool or cotton. The filaments 44 are clamped to the block 40 by four clamping blocks 46a to 46d, which are seated in corresponding recesses 48a to 48d, respectively, of the block 40 and are fixed by screws. The filaments 44 are attached to the disks 10a, 12a by being led through corresponding holes of the discs and knotted. Alternatively the filaments may consist of plastics, as polyamide or any other suitable non-metallic material. Other devices such as nets or films made of materials of the above mentioned type may be used as a mechanical support of low heat conductivity for the sample holders.

Each sample holder 10a, 12a is provided with a heating device 50a, 50b, respectively, and a temperature sensor 52a and 52b, respectively. The heating devices and the temperature sensors are positioned on the lower side of the disks which is shown in FIG. 4. The upper sides of the disks, which cannot be seen in FIG. 4, is plane and serves as support for the respective samples.

In the present embodiment, the heating devices 50a, 50b each comprise a meander-shaped electric resistance element formed by vacuum deposition of a Ni-Cr alloy and having a resistance of about 1500 ohms at room temperature.

The temperature sensor may be a germanium temperature sensor, a thermo couple or a platinum resistance element or any other known temperature sensing device.

A platinum (or germanium) resistance etalon 58 positioned in a bore of the block 40 is used for an accurate measurement of the temperature $T_0(t)$ of the block.

The terminals of the heating devices and the temperature sensors on the disks 10a, 12a are provided with terminal pads which are electrically coupled to a multi-terminal connector 56 by thin electrical wires 54a, 54b. The wires 54a, 54b may be 20 micron gold wires connected to the terminal pads by pressure welding and form heat conduction paths. The connector 56 is positioned in a corresponding recess of the block 40 and may comprise a series of pads to which the gold wires are connected by a pressure welding. The connector is coupled by a multi-conductor cable to a control and signal processing unit of known type (not shown).

In an exemplary embodiment, the copper block 40 has an outer diameter of 50 mm. The disks 10a, 12a are made of sapphire and have a thickness of 0.15 mm and a diameter of 8 mm. The heat capacity of these disks at 4 K. is in the order of microjoules. The typical accuracy of measurement is about 1%. The described calorimeter can have a resolution of 10 nJ and less with sample masses in the order of milligrams in a temperature range down to 1 K. and below.

The course of a typical measuring cycle is essentially as follows: A measuring sample is positioned on the upper side of the disk 10a, and a reference sample is positioned on the upper side of the disk 12a. The area of heat contact of the sample with the supporting disk should be as large as possible. A substance, such as a thin layer of apiezone grease, may be provided between the disk and the sample to improve the heat transfer. As mentioned, the conditions are preferably chosen so that the duration of each heat pulse and the time needed for establishing a sufficient temperature equilibrium in the respective systems is short relative to the heat relaxation time constant $t_i^*$.

As shown in FIG. 5, the system 60 of FIG. 4 is then positioned on a cooling head 62 of a cryostat 64. The exemplary cryostat 64 shown in FIG. 5 is a helium flow or evaporation cryostat which is supplied with liquid helium. A supply line 66 connects a chamber within the cooling head 62 with a liquid helium supply 68, e.g. a 50 liter Dewar container. Gaseous helium produced by evaporation in the cooling head 62 flows through an outlet conduit 70 into a cooling coil 72 attached to a cylindrical heat shield 74, which concentrically surrounds the cooling head 62 and the measuring system 60 in spaced relationship. The outlet end of the coil 72 is connected to a vacuum pump 80 through a conduit 76 which contains a throttle valve 78. The vacuum pump 80 in combination with the throttle valve 78 allow a variation of the evaporation pressure of the helium within the cooling head 62 and, thus, a gross adjustment of the cooling head temperature. The cooling head is provided with an electronically regulated heating device 82 for fine adjustment of the cooling head temperature. The heating device 82 is controlled by a signal depending on the temperature $T_0(t)$ of the block 40. The temperature signal may be provided by the temperature sensor 58. The temperature of the copper block 40 and, thus, the environment temperature $T_0(t)$ can be adjusted with a cryostat of this known type with an accuracy within about 1/1000 K. and varied according to a desired, e.g., linear function of time within any desired range from about few Kelvins to 120 K. and more.

Various changes and modifications to the above described embodiment which are within the scope of the appended claims will occur to those skilled in the art.

We claim:

1. A method for determining the heat capacity of a sample, said method comprising the steps of:
   (a) providing a measuring system including said sample and sample support means, said measuring system having a first heat capacity and a sample heat relaxation time constant;
   (b) providing a reference system including a reference sample and reference sample support means, said reference system having a second heat capacity and a reference heat relaxation time constant;
   (c) providing an environment of controllable temperature;
   (d) coupling said measuring system to said environment through a first heat conducting path having a predetermined first heat resistance;
   (e) coupling said reference system to said environment through a second heat conducting path having a predetermined second heat resistance;
   (f) increasing the temperature of said environment from a predetermined initial temperature in accordance with a predetermined function of time;
   (g) supplying heat energy of a predetermined first amount to said measuring system and essentially simultaneously applying heat of a predetermined second amount to said reference system, whereby the heat is applied to said systems during a first period of time which is small compared with the heat relaxation time constants resulting from the heat capacity and the heat conduction path resistance of each system;
   (h) determining the temperatures of said measuring and reference systems and of said environment at least during a predetermined second period of time following the application of heat energy in step (g) to measure the heat capacity of the sample, and
   (i) repeating the method of steps (g) and (h) after a third period of time which is at least on the order of magnitude of said heat relaxation time constants.

2. A method as claimed in claim 1, wherein the heat capacity of said measuring system is on the same order of magnitude as the heat capacity of said reference system.

3. The method as claimed in claim 1 wherein said first and second heat resistances are at least approximately equal.

4. The method as claimed in claim 1, wherein said first and second amounts of heat energy are at least approximately equal.

5. The method as claimed in claim 1, wherein in step (h) the temperature difference between the measuring system and the reference system and the temperature difference between one of said systems and the environment are measured.

6. The method as claimed in claim 1, wherein said temperature is measured continuously during the second predetermined period of time.

7. A method as claimed in claim 1 wherein the temperature increase in step (f) is linear.

8. A method as claimed in claim 7 wherein the temperature increase in step (f) is continuous.

9. An isoperibol twin calorimeter comprising:
   (a) a body of controllable temperature for defining an environment temperature;
   (b) sample support means disposed within the body;
   (c) reference sample support means disposed within the body;
   (d) means for heating said sample support means;
   (e) means for heating said reference sample support means;
   (f) a first heat conduction path of predetermined heat resistance between said sample support means and said body;
   (g) a second heat conducting path of predetermined second heat resistance between said reference sample support means and said body;
   (h) means connected to the sample support means for producing a signal depending on the temperature of said sample support means;
   (i) means connected to the reference support means for producing a signal depending on the temperature of said reference sample support means;
   (j) means connected to the body for producing a signal depending on the temperature of said body;
   (k) means for increasing the temperature of said body in accordance with a predetermined function of time;
   (l) means for repeatedly energizing each of said heating means, the repetition being short as compared to the time of each energization, and
   (m) means for deriving signals which are functions of the temperatures of said sample support means and said reference sample support means and said body, respectively.

10. The calorimeter as claimed in claim 9, wherein each of said sample support means comprises a thin, disk-shaped member, means for mechanically supported the member from said body of controllable temperature by means of low heat conductivity, and wherein thin electrical wires are provided which connect terminals on each of said members with terminals on said body, said wires forming said heat conducting paths.

11. The calorimeter as claimed in claim 10, wherein said disk-shaped members are made of sapphire.

12. The calorimeter as claimed in claim 10, wherein said disk-shaped members are made of germanium.

13. The calorimeter as claimed in claim 10, wherein said mechanical support means are filaments made of a non-metallic material.

14. The calorimeter as claimed in claim 9 wherein temperature increase is linear.

15. The calorimeter as claimed in claim 14 wherein the temperature increase is continuous.

* * * * *